(12) United States Patent
Yukumoto et al.

(10) Patent No.: US 10,414,118 B2
(45) Date of Patent: *Sep. 17, 2019

(54) MICROCHIP MANUFACTURED WITH THERMOCOMPRESSION

(71) Applicant: Sony Corporation, Tokyo (JP)

(72) Inventors: Tomomi Yukumoto, Tokyo (JP); Takeshi Yamasaki, Tokyo (JP); Shoji Akiyama, Tokyo (JP); Yuji Akiyama, Tokyo (JP)

(73) Assignee: SONY CORPORATION, Tokyo (JP)

( * ) Notice: Subject to any disclaimer, the term of this patent is extended or adjusted under 35 U.S.C. 154(b) by 181 days.

This patent is subject to a terminal disclaimer.

(21) Appl. No.: 15/444,906

(22) Filed: Feb. 28, 2017

(65) Prior Publication Data
US 2017/0203296 A1 Jul. 20, 2017

Related U.S. Application Data

(63) Continuation of application No. 14/131,730, filed as application No. PCT/JP2012/003939 on Jun. 15, 2012, now Pat. No. 9,610,750.

(30) Foreign Application Priority Data

Jul. 20, 2011 (JP) .................. 2011-158723

(51) Int. Cl.
*B32B 3/20* (2006.01)
*B32B 3/26* (2006.01)
(Continued)

(52) U.S. Cl.
CPC .......... *B32B 3/30* (2013.01); *B01L 3/502707* (2013.01); *B01L 3/502715* (2013.01);
(Continued)

(58) Field of Classification Search
CPC ......... B01D 2221/10; B03C 7/12; B03C 9/00; B03C 2201/02; B03C 2201/18;
(Continued)

(56) References Cited

U.S. PATENT DOCUMENTS

| 5,085,605 A | 2/1992 | Itani et al. |
| 5,427,663 A | 6/1995 | Austin et al. |

(Continued)

FOREIGN PATENT DOCUMENTS

| CN | 1687766 A | 10/2005 |
| CN | 1745264 A | 3/2006 |

(Continued)

OTHER PUBLICATIONS

Chinese Office Action (with English translation) dated Jul. 4, 2016 in corresponding Chinese application No. 2015104200586 (14 pages).

(Continued)

*Primary Examiner* — Megha M Gaitonde
(74) *Attorney, Agent, or Firm* — K&L Gates LLP

(57) ABSTRACT

There is provided a microchip including at least two substrates each comprising a thermoplastic resin, and at least one member comprising a material having a heat distortion temperature higher than a heat distortion temperature of the thermoplastic resin, the at least one member including at least one engagement end including a protrusion extending between the at least two substrates, wherein the at least one member is fixed to the at least two substrates by the protrusion being held between the at least two substrates by at least one wall surface that is thermally deformed by thermocompression.

20 Claims, 8 Drawing Sheets

(51) Int. Cl.
  B32B 3/30 (2006.01)
  B32B 27/08 (2006.01)
  B32B 3/08 (2006.01)
  B01L 3/00 (2006.01)
  G01N 21/51 (2006.01)
  G01N 21/64 (2006.01)

(52) U.S. Cl.
  CPC ............... B32B 3/08 (2013.01); B32B 3/266 (2013.01); B32B 27/08 (2013.01); G01N 21/51 (2013.01); B01L 2200/0636 (2013.01); B01L 2200/0689 (2013.01); B01L 2200/12 (2013.01); B01L 2300/0645 (2013.01); B01L 2300/0654 (2013.01); B01L 2300/0816 (2013.01); B01L 2300/0838 (2013.01); B01L 2300/0877 (2013.01); B01L 2300/0887 (2013.01); B32B 2307/412 (2013.01); G01N 21/645 (2013.01); G01N 2021/513 (2013.01); G01N 2021/6482 (2013.01); G01N 2201/06113 (2013.01); Y10T 428/24612 (2015.01)

(58) Field of Classification Search
  CPC .................. B03C 2201/20; B03C 5/00; Y10T 428/24174; Y10T 428/24479; Y10T 428/24612; Y10T 428/24744; Y10T 428/24562; B01L 3/50; G01N 15/00; G01N 15/14; G01N 21/00; B32B 3/02; B32B 3/08; B32B 3/20; B32B 3/26; B32B 3/263; B32B 3/30; B32B 27/06; B32B 27/08; B32B 37/04; B32B 37/16; B32B 37/18; B32B 37/182; B32B 37/185; B29C 43/003; B29C 43/02; B29C 43/021; B29C 43/10; B29C 43/18; B29C 43/20; B29C 43/203; B29C 43/206; B29C 43/52; B29C 2043/181; B29C 2043/182; B29C 2043/189; B29C 51/002; B29C 51/12; B29C 51/14; B29C 51/42; B29C 51/421; B29C 65/02; B29C 70/68; B29C 70/685; B29C 70/70; B29C 70/72; B29C 70/742

USPC ....... 428/131–140, 156, 161, 166, 172, 188; 264/248, 249; 204/600; 209/3.1–3.3, 209/539, 546, 576, 579, 638, 656, 155; 210/806, 767
  See application file for complete search history.

(56) References Cited

U.S. PATENT DOCUMENTS

| | | | |
|---|---|---|---|
| 7,417,734 | B2 | 8/2008 | Kanda |
| 7,880,108 | B2 | 2/2011 | Schembri et al. |
| 8,795,500 | B2 | 8/2014 | Shinoda |
| 2002/0078590 | A1* | 6/2002 | Collins .................. A43B 7/06 36/3 R |
| 2002/0085202 | A1 | 7/2002 | Gordon |
| 2002/0176804 | A1 | 11/2002 | Strand et al. |
| 2005/0109396 | A1 | 5/2005 | Zucchelli et al. |
| 2006/0214101 | A1 | 9/2006 | Takahashi |
| 2010/0037483 | A1* | 2/2010 | Meschter ................. A43B 3/26 36/47 |
| 2010/0096563 | A1 | 4/2010 | Ponjee et al. |

FOREIGN PATENT DOCUMENTS

| | | |
|---|---|---|
| JP | H04503640 | 7/1992 |
| JP | H09504362 | 4/1997 |
| JP | 2000348155 | 12/2000 |
| JP | 2007170958 | 7/2007 |
| JP | A 2007-263706 | 10/2007 |
| JP | 2009243965 | 10/2009 |
| JP | 2010-190680 | 9/2010 |
| WO | 2006/123267 | 11/2006 |
| WO | 2010095391 | 8/2010 |

OTHER PUBLICATIONS

Office Action issued in JP Application 2011158723 dated Mar. 8, 2016 (11 pages).
Office Action issued in JP Application 2011-158723 dated Aug. 27, 2015 (11 pages).

* cited by examiner

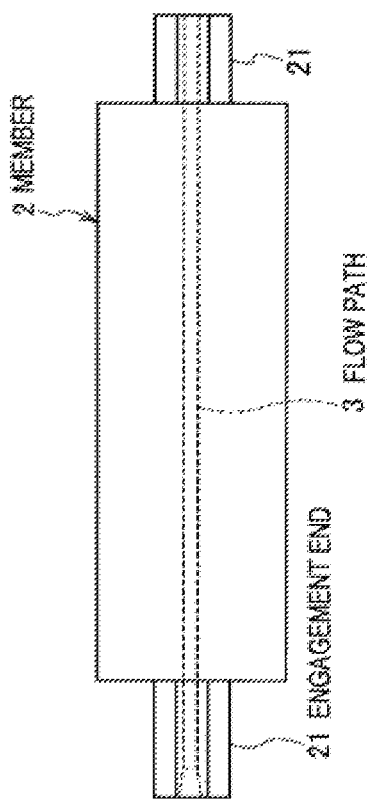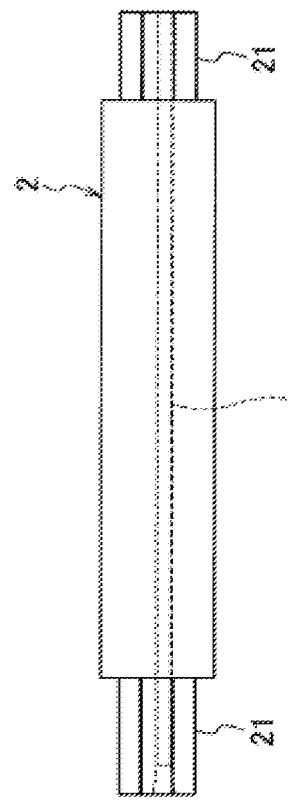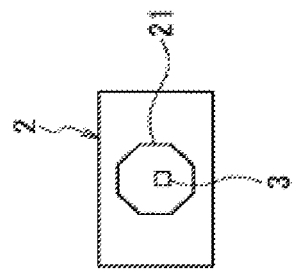

MICROCHIP MANUFACTURED WITH THERMOCOMPRESSION

CROSS REFERENCES TO RELATED APPLICATIONS

The present application is a continuation of U.S. application Ser. No. 14/131,730, filed Jan. 9, 2014, granted as U.S. Pat No. 9,610,750 entitled, "Composite Structure and Manufacturing Method Therefor," which is a national stage of International Application No. PCT/JP2012/003939, filed on Jun. 15, 2012, and claims priority to Japanese Patent Application No. 2011-158723 filed on Jul. 20, 2011, the disclosure of which is incorporated herein by reference.

BACKGROUND

The present technology relates to a composite structure and a manufacturing method therefor. More specifically, the present technology relates to a composite structure that is formed such that a plurality of members made of materials having different heat distortion temperatures are combined utilizing thermal deformation, and to a manufacturing method therefor.

In recent years, microchips are being developed in which ultra-precision machining technology of the semiconductor industry is applied, and a region or a flow path for chemical or biological analysis is provided on a substrate made of silicon or glass. An analysis system using this kind of microchip is referred to as a micro total analysis system (micro-TAS), a lab-on-chip system or a biochip system. The analysis system is attracting attention as a technology that can speed up the analysis, improve efficiency or promote integration, and further can reduce the size of an analyzing device.

With micro-TAS, the analysis can be made using a small sample amount, and the microchip is disposable. For these reasons, the micro-TAS is expected to be applied, particularly, to biological analysis that uses valuable micro samples and many test substances. For example, an electrochemical detector for liquid chromatography and a small electrochemical sensor in clinical practice are known as application examples of micro-TAS.

Further, as another application example, a micro-particle analysis technology is known that optically, electrically or magnetically analyzes characteristics of micro-particles, such as cells or micro beads, in the flow path disposed in the microchip. In the micro-particle analysis technology, a population (a group) that is determined to satisfy a predetermined condition by the analysis is separated and collected from the micro-particles.

For example, Patent Literature 1 (Japanese Patent Application Publication No. 2010-190680) discloses "a microchip that includes: a flow path through which liquid containing micro-particles flows; and an orifice from which the liquid flowing through the flow path is discharged to a space outside the chip, wherein a light irradiated portion to detect optical characteristics of the micro-particles is formed at a predetermined section of the flow path". This microchip controls a movement direction of a liquid droplet containing the micro-particles discharged from the orifice. Thus, the microchip is used to separate and collect the micro-particles that are determined, at the light irradiated portion, to have a predetermined optical characteristic.

SUMMARY

When the microchip is formed by combining a plurality of members, it is necessary to highly accurately position flow paths or regions that are formed in the respective members and to connect them together. As a method for positioning the flow paths etc., in related art, a very troublesome method is used in which the flow paths etc. of the respective members are connected while observing them using a microscope.

In light of the above, it is a main object of the present technology to provide a composite structure that makes it possible to highly accurately and easily position flow paths or regions that are formed in respective members and to connect them together.

In order to solve the above-described problems, the present technology provides a composite structure including: at least two substrates which are made of thermoplastic resin and which are bonded by thermocompression; and at least one member which is made of a material whose heat distortion temperature is higher than a heat distortion temperature of the thermoplastic resin and which is inserted into a space formed in at least one of the substrates. The member inserted in the space is fixed and held by wall surfaces which form the space of the substrates and which are thermally deformed by thermocompression.

In the composite structure, regions that are respectively formed in at least one of the substrates and in the member are linked and connected together by determining a position of the member in the space by the thermally deformed wall surfaces.

The composite structure may be a microchip including a flow path which is formed as the regions and through which liquid passes. The composite structure may further include a light irradiated portion where light is irradiated onto one of the liquid that flows through the flow path and a sample contained in the liquid. In this case, it is preferable that the light irradiated portion is formed by the member made of a material having optical transparency that is superior to that of the thermoplastic resin that forms the substrates.

Further, the present technology provides a manufacturing method of a composite structure, including: arranging at least two substrates which are made of thermoplastic resin and which have a space that is formed in at least one of the substrates; inserting, into the space, at least one member that is made of a material whose heat distortion temperature is higher than a heat distortion temperature of the thermoplastic resin; and bonding the substrates by thermocompression and thereby causing wall surfaces, which form the space of the substrates and which are thermally deformed, to fix and hold the member inserted in the space.

With the manufacturing method of the composite structure, regions that are respectively formed in at least one of the substrates and in the member can be linked and connected together by determining a position of the member in the space by the thermally deformed wall surfaces.

In the manufacturing method of the composite structure, the thermocompression of the substrates is performed at a temperature which is higher than the heat distortion temperature of the thermoplastic resin that forms the substrates and which is lower than the heat distortion temperature of the material that forms the member.

With the present technology, a microchip is provided that makes it possible to highly accurately and easily position flow paths or regions that are formed in respective members and to connect them together.

BRIEF DESCRIPTION OF THE FIGURES

Additional features and advantages are described herein, and will be apparent from the following Detailed Description and the figures.

FIGS. 5(A) to 5(C) show schematic views illustrating a configuration of a member 2, where (A) shows a top view, (B) shows a side view and (C) shows a front view.

DETAILED DESCRIPTION

Figure 1:
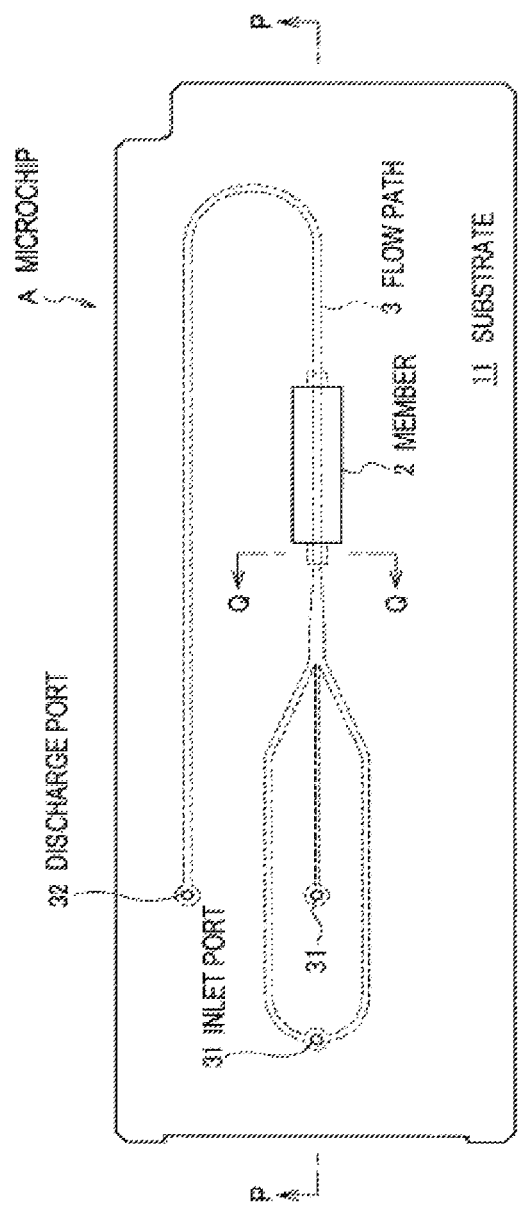
FIG. 1 is a top schematic view illustrating a configuration of a composite structure according to the present technology.
Figure 2:
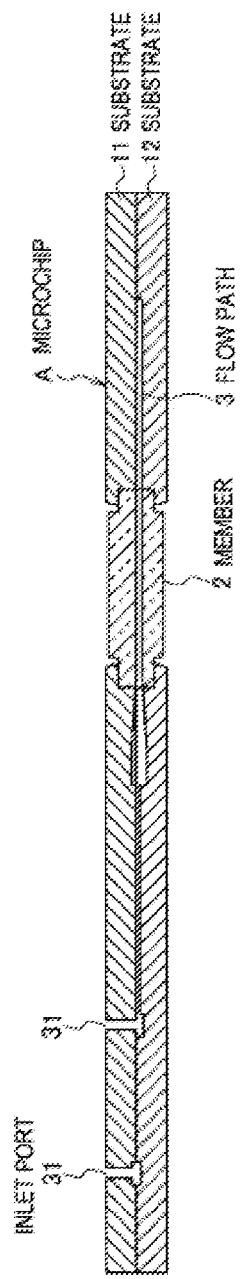
FIG. 2 is a cross-sectional schematic view (a cross section taken along a line P-P in FIG. 1) illustrating the configuration of the composite structure according to the present technology.
Figure 3:
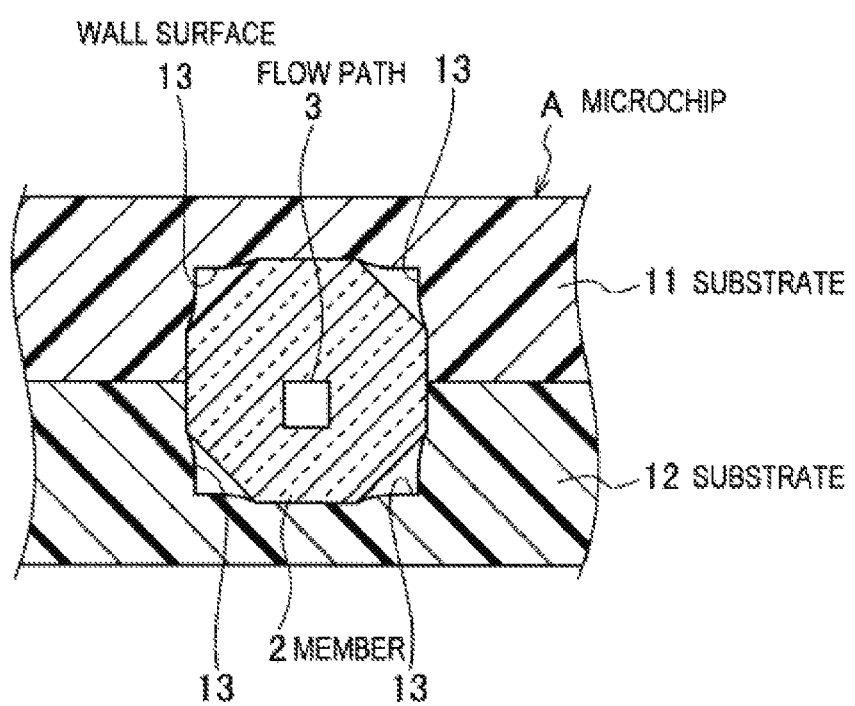
FIG. 3 is a cross-sectional schematic view (a cross section taken along a line Q-Q in FIG. 1) illustrating the configuration of the composite structure according to the present technology.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted. The explanation will be made in the following order.
1. Composite structure
2. Manufacturing method of composite structure
3. Microchip for analyzing micro-particles 1. Composite Structure FIG. 1 is a top schematic view illustrating a configuration of a composite structure according to the present technology. FIG. 2 and FIG. 3 are cross-sectional schematic views each illustrating the configuration of the composite structure according to the present technology. FIG. 2 corresponds to a cross section taken along a line P-P in FIG. 1, and FIG. 3 corresponds to a cross section taken along a line Q-Q in FIG. 1.

The composite structure denoted by a reference numeral A in the drawings is provided with substrates 11 and 12 that are bonded by thermocompression, and an embedded member 2 (hereinafter simply referred to as the "member 2") that is embedded in and bonded to the substrates 11 and 12. A region 3 is formed in the substrates 11 and 12 and the member 2. Hereinafter, the region 3 is explained as a flow path through which liquid passes, and is referred to as the "flow path 3". Further, the composite structure A is explained as a microchip that is provided for analyzing the liquid, and is referred to as the "microchip A".

The substrates 11 and 12 are made of thermoplastic resin and bonded by thermocompression. As structural elements of the flow path 3, inlet ports 31, which introduce liquid to be analyzed or liquid containing an analysis target object into the flow path 3 from the outside, and a discharge port 32, which discharges the liquid from the inside of the flow path 3 to the outside, are formed in the substrates 11 and 12.

The thermoplastic resin may be a known resin that is used as a microchip material. Examples of the thermoplastic resin include polycarbonate, polymethyl methacrylate (PMMA) resin, cyclic polyolefin, polyethylene, polystyrene, polypropylene and polydimethylsiloxane (PDMS). The formation of the flow path 3 etc. in the substrates 11 and 12 can be performed using a known technique, such as nanoimprinting, injection molding, machining or the like.

The member 2 is made of a material whose heat distortion temperature is higher than that of the thermoplastic resin that forms the substrates 11 and 12. Examples of the material of the member 2 include the aforementioned thermoplastic resins, metal, glass, quartz, ceramic and the like. For example, when the member 2 is made of glass, the formation of the flow path 3 etc. in the member 2 can be performed by wet etching or dry etching. Further, for example, when the member 2 is made of metal, the formation of the flow path 3 etc. can be performed by machining.

As shown in FIG. 1 and FIG. 2, a section of the flow path 3 that is formed in the substrates 11 and 12 and a section of the flow path 3 that is formed in the member 2 are linked and connected together without displacement occurring. Thus, the liquid introduced into the flow path 3 can flow through the flow path 3 without any disturbance in the flow occurring at a joint between the section formed in the substrates 11 and 12 and the section formed in the member 2.

The connecting together of the flow path 3 formed in the substrates 11 and 12 and the flow path 3 formed in the member 2 can be achieved by positioning the member 2 with respect to the substrates 11 and 12 utilizing thermal deformation of the substrates 11 and 12 that is generated during thermocompression bonding. More specifically, as shown in FIG. 3, in the microchip A, the member 2 is fixed and held by wall surfaces 13 of the substrates 11 and 12 that have contracted due to thermal deformation, so that the substrates 11 and 12 and the member 2 are positioned. The positioning of the substrates 11 and 12 and the member 2 that is performed utilizing thermal deformation of the substrates 11 and 12 will be explained in more detail in the next section, "Manufacturing method of composite structure".

Here, the composite structure formed by combining the two substrates 11 and 12 and the single member 2 is exemplified as the microchip A. However, the composite structure according to the present technology may include three or more substrates and may also include two or more members. Further, here, an example is explained in which the region, such as the flow path 3 etc., is formed in each of the substrates 11 and 12. However, these regions may be all formed in one of the substrates 11 and 12.

2. Manufacturing Method of Composite Structure

Figure 4:
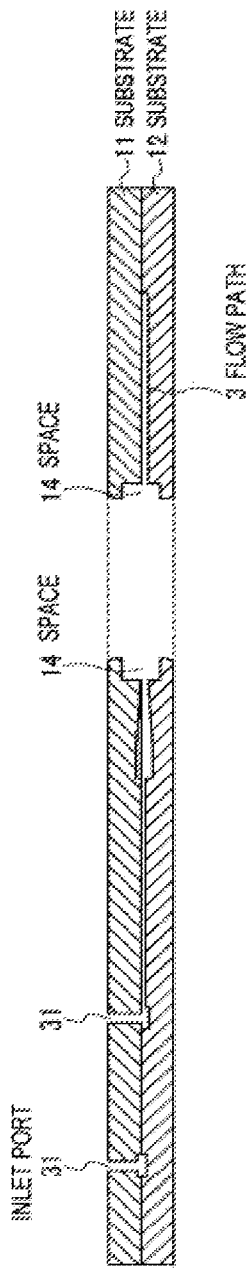
FIG. 4 is a cross-sectional schematic view illustrating a configuration of substrates 11 and 12.
Figure 6A:
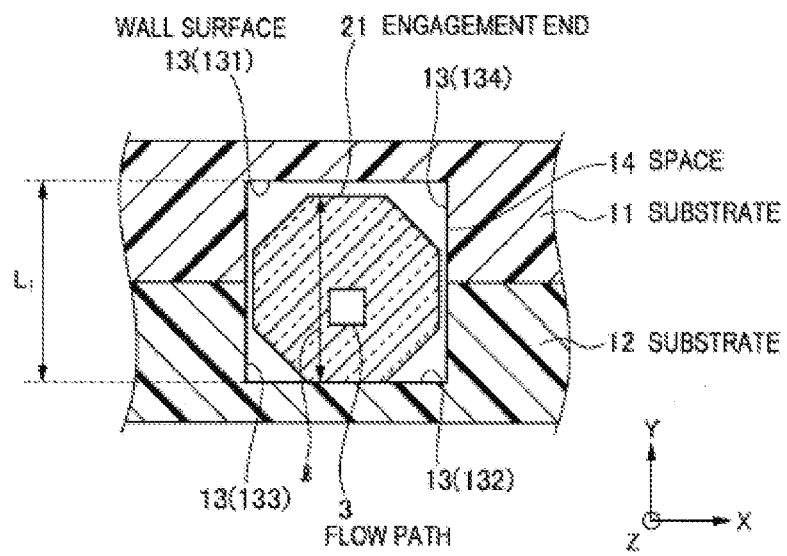
FIGS. 6(A) and 6(B) show cross-sectional schematic views illustrating a configuration of a bonding portion between the member 2 and the substrates 11 and 12, where (A) shows the substrates 11 and 12 before thermal deformation and (B) shows the substrates 11 and 12 after thermal deformation.
Figure 6B:
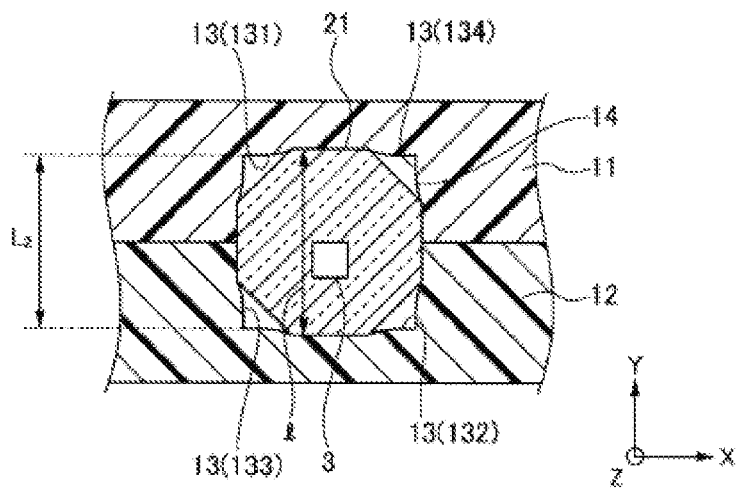
Figure 7A:
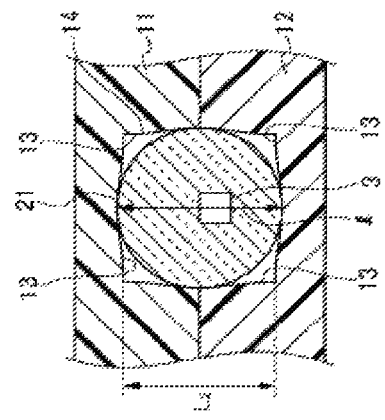
FIGS. 7(A) to 7(D) show cross-sectional schematic views illustrating a configuration of a modified example of the bonding portion between the member 2 and the substrates 11 and 12, where (A) and (C) show the substrates 11 and 12 before thermal deformation and (B) and (D) show the substrates 11 and 12 after thermal deformation.
Figure 7B:
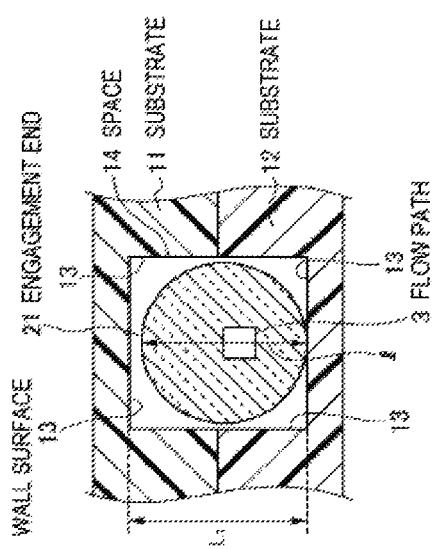
Figure 7C:
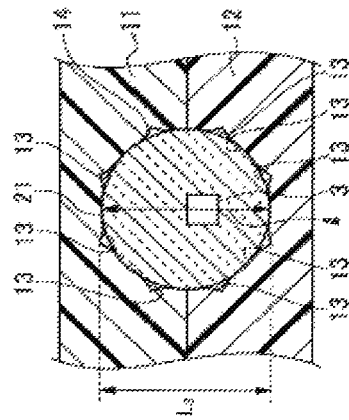
Figure 7D:
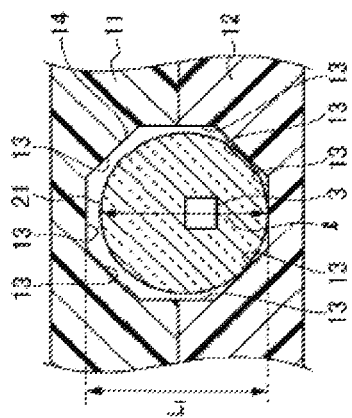

Next, a manufacturing method of the composite structure according to the present technology will be explained with reference to FIG. 4 to FIG. 6, taking the above-described microchip A as an example. FIG. 4 is a cross-sectional schematic view illustrating a configuration of the substrates 11 and 12. FIG. 4 corresponds to FIG. 2 except that the member 2 is omitted. FIG. 5 shows schematic views illustrating a configuration of the member 2, where (A) shows a top view, (B) shows a side view and (C) shows a front view. FIG. 6 shows cross-sectional schematic views illustrating a configuration of a bonding portion between the member 2 and the substrates 11 and 12, where (A) shows the substrates 11 and 12 before thermal deformation and (B) shows the substrates 11 and 12 after thermal deformation. Note that FIG. 6 corresponds to the cross section taken along the line Q-Q in FIG. 1.

Firstly, a first process will be explained. In the first process, the substrates 11 and 12 made of thermoplastic resin and having spaces 14 are arranged. In the first process, the spaces 14 are formed in the substrates 11 and 12 such that the member 2 can be inserted into the spaces 14 in a state in which the substrates 11 and 12 are overlapped with each other (refer to FIG. 4). When the substrates 11 and 12 are overlapped with each other, each of the spaces 14 is a rectangular parallelepiped shaped space that has a surface from which the flow path 3 opens and an opposing surface that is open. In a similar manner to the flow path 3, the spaces 14 are formed using a technique, such as nanoimprinting, injection molding, machining or the like.

Engagement ends 21 that are inserted into the spaces 14 of the substrates 11 and 12 are formed on both ends of the member 2. The engagement ends 21 are formed each including a protrusion which may be in an octagonal prism shape, and the protrusion may have an octagonal shape (refer to FIG. 5 (C)) in a front view. The engagement ends 21 are provided on both ends of a main body of the member 2 that has a rectangular parallelepiped shape. The single flow path 3 is formed in the main body of the member 2 and in the two engagement ends 21.

Next, a second process will be explained. In the second process, the member 2 formed of a material whose heat distortion temperature is higher than that of the above-described thermoplastic resin is inserted into the spaces 14. In the second process, the engagement ends 21 are inserted into the spaces 14 formed by the overlapped substrates 11 and 12. FIG. 6 (A) shows a state in which the engagement ends 21 are inserted into the spaces 14. The insertion of the engagement ends 21 into the spaces 14 may be performed such that, after the substrate 11 and the substrate 12 are overlapped with each other, the engagement ends 21 are inserted into the spaces 14. However, the insertion can preferably be performed in the following manner. That is, first, the engagement ends 21 of the member 2 are engaged with recessed portions of the substrate 12 that form the spaces 14. Next, the substrate 11 is overlapped with the substrate 12 such that positions of recessed portions of the substrate 11 that form the spaces 14 match positions of the engagement ends 21 engaged with the substrate 12.

In order to easily insert the engagement ends 21 into the spaces 14, it is preferable that an inner diameter $L_1$ of the spaces 14 is equal to or slightly larger than an outer diameter 1 of the engagement ends 21. Note that, even when the inner diameter $L_1$ of the spaces 14 is larger than the outer diameter 1 of the engagement ends 21, it is necessary for the wall surfaces 13, which form the spaces 14 and which are thermally deformed when the substrates 11 and 12 are bonded by thermocompression, to be able to come into contact with the engagement ends 21, as explained next. Note that, here, the inner diameter $L_1$ and the outer diameter 1 are not to be understood exclusively as those in a vertical direction (a Y-axis direction) in FIG. 6, but are to be understood as the diameters in any direction including a horizontal direction (an X-axis direction).

Next, a third process will be explained. In the third process, the substrates 11 and 12 are bonded by thermocompression and thus the member 2 inserted in the spaces 14 is fixed and held by the wall surfaces 13 that form each of the spaces 14 of the thermally deformed substrates 11 and 12. In the third process, after the engagement ends 21 are inserted into the spaces 14, the substrates 11 and 12 are bonded by thermocompression. The thermocompression bonding is performed at a temperature that is higher than the heat distortion temperature of the thermoplastic resin that forms the substrates 11 and 12 and is lower than the heat distortion temperature of the material that forms the member 2. As a result of this thermocompression operation, the substrates 11 and 12 are thermally deformed, the wall surfaces 13 that form the spaces 14 thermally contract, and the spaces 14 contract. On the other hand, the member 2 does not thermally contract as a result of the thermocompression operation. Thus, an inner diameter $L_2$ of the spaces 14 after the thermal deformation becomes smaller than the outer diameter 1 of the engagement ends 21, and each of the engagement ends 21 is fixed and held by the thermally contracted wall surfaces 13, as shown in FIG. 6 (B). Thus, the substrates 11 and 12 and the member 2 are bonded together.

When the thermocompression operation is performed, the thermal contraction of the wall surfaces 13 and the contraction of the spaces 14 occur in an isotropic manner. Specifically, four of the wall surfaces 13 that form each of the spaces 14, namely, wall surfaces 131 and 132 that face each other in the Y-axis direction and wall surfaces 133 and 134 that face each other in the X-axis direction, expand uniformly to the space 14 side as a result of the thermal contraction. Thus, each of the engagement ends 21 is held at the center in the space 14 and is positioned by the wall surfaces 131, 132, 133 and 134 that expand by the same amount. Then, the section of the flow path 3 formed in the substrates 11 and 12 and the section of the flow path 3 formed in the member 2 are linked and connected together (refer to FIG. 1 and FIG. 2)

In this manner, the thermal contraction of the substrates 11 and 12 is utilized to hold and fix the member 2 at the center in the spaces 14. Thus, the sections of the flow path 3 that are respectively formed in the member 2 and in the substrates 11 and 12 can be easily and highly accurately positioned and connected together without displacement occurring.

The inner diameter $L_1$ of the spaces 14 and the outer diameter 1 of the engagement ends 21 are set to appropriate diameters so that the thermally contracted wall surfaces 13 can come into close contact with each of the engagement ends 21, taking account of a thermal contraction amount of the wall surfaces 13 formed in this manner. More specifically, the inner diameter $L_1$ of the spaces 14 is designed in advance such that the inner diameter $L_2$ after the thermal deformation is smaller than the outer diameter 1 of the engagement ends 21.

Here, a case is explained in which positioning of each of the engagement ends 21 is performed inside the space 14 in both the X-axis direction and the Y-axis direction. However, the positioning may be performed in only one direction, namely, only in the X-axis direction by the wall surfaces 131 and 132 or only in the Y-axis direction by the wall surfaces 133 and 134. When the positioning is performed in only one direction, the inner diameter $L_1$ of the spaces 14 in the X-axis direction may be different from that in the Y-axis direction and, in a similar manner, the outer diameter 1 of the engagement ends 21 in the X-axis direction may be different from that in the Y-axis direction. Further, the positioning can be performed in a Z-axis direction (in a direction that is parallel to the flow path 3) in addition to the X-axis direction and/or the Y-axis direction.

Further, it is preferable to design the shape of the spaces 14 and the shape of the engagement ends 21 such that some areas of the wall surfaces 13 do not come into contact with each of the engagement ends 21 when the wall surfaces 13 thermally contract. If whole areas of the wall surfaces 13 come into close contact with each of the engagement ends 21 when the wall surfaces 13 thermally contract, there is a risk that the member 2 is deformed and damaged by pressure of the thermoplastic resin that expands to the space 14 side. In order to avoid this, here, the spaces 14 are formed in a rectangular parallelepiped shape and the engagement ends 21 include protrusions that are formed in an octagonal prism shape. Thus, when the spaces 14 thermally contract, four of the eight surfaces of each of the protrusion of the engagement ends 21 do not come into contact with the wall surfaces 13 and gaps are formed between the wall surfaces 13 and the four surfaces. As a result, these gaps serve as escapes for the expanded thermoplastic resin and inhibit an excessive pressure from being applied to the member 2.

The shape of the spaces 14 and the shape of the engagement ends 21 are not limited to a combination of a rectangular parallelepiped shape and an octagonal prism shape, and may be a combination of various shapes. For example, as shown in FIG. 7 (A) and FIG. 7 (B), the shape of the engagement ends 21 may be a cylindrical shape. Further, for example, as shown in FIG. 7 (C) and FIG. 7 (D), the spaces 14 may have an octagonal prism shape and the engagement ends 21 may have a cylindrical shape. In either case, when the wall surfaces 13 thermally contract, some areas of the wall surfaces 13 come into close contact with each of the engagement ends 21 and function to position each of the engagement ends 21 in the spaces 14, while the other areas of the wall surfaces 13 form gaps with each of the engagement ends 21 and function to inhibit an excessive pressure being applying to the member 2.

In order to improve liquid tightness, a sealant may be arranged or processing using a sealant may be performed on the bonding portion between the substrates 11 and 12 and the member 2 that are bonded utilizing the thermal deformation of the substrates 11 and 12. Sealing can be performed by a method in which an elastic member (an O-ring etc.) made of rubber or the like is arranged on the bonding portion, a method in which an adhesive is applied to the bonding portion, or the like.

3. Microchip for Analyzing Micro-Particles

As a specific example of an embodiment of the above-described microchip A, an example will be explained in which the microchip A is used for analyzing micro-particles. Note that the above-described Patent Literature 1 can be referred to as the microchip for analyzing micro-particles In the microchip A shown in FIG. 8, the member 2 made of crystal is embedded in a thermoplastic resin substrate that is formed by bonding substrates by thermocompression. The flow path 3, through which flows a liquid (hereinafter referred to as a "sample liquid") containing micro-particles to be analyzed, is formed in the substrate and the member 2.

The sample liquid is introduced into the flow path 3 from a sample inlet 311. The micro-particles contained in the sample liquid may be biologically-relevant micro-particles, such as cells, microorganisms and liposomes, or may be synthetic particles such as latex particles, gel particles and industrial particles. The biologically-relevant micro-particles include chromosomes that form various types of cells, liposomes, mitochondria and organelles. The cells to be targeted include animal cells (hematopoietic cells etc.) and plant cells. The microorganisms include bacteria such as coli bacteria, viruses such as tobacco mosaic virus, fungi such as yeast, and the like. Further, it is assumed that the biologically-relevant micro-particles can include biologically-relevant polymers, such as nucleic acid, protein and a complex of nucleic acid and protein. Further, the industrial particles may be, for example, organic or inorganic polymer materials, metals, or the like. The organic polymer materials include polystyrene, styrene-divinylbenzene, polymethyl methacrylate, and the like. The inorganic polymer materials include glass, silica, magnetic materials, and the like. The metals include gold colloid, aluminum, and the like. Normally, the shape of these particles is a sphere. However, these particles may have a shape other than a sphere, and the size and mass of these particles are not particularly limited.

The sample liquid is fed through the flow path 3 in a state in which the sample liquid is surrounded by a sheath liquid that is introduced from a sheath inlet 312. The sheath liquid introduced from the sheath inlet 312 is divided into streams in two directions and fed. After that, at a confluence portion with the sample liquid introduced from the sample inlet 311, the sheath liquid joins the sample liquid such that the streams of the sheath liquid sandwich the sample liquid from two directions. Thus, a three-dimensional laminar flow is formed at the confluence portion such that a sample liquid laminar flow is located in the center of a sheath liquid laminar flow.

A reference numeral 4 denotes a suction flow path. When clogging or air bubbles occur in the flow path 3, the suction flow path 4 temporarily reverses the flow by applying a negative pressure to the inside of the flow path 3 in order to resolve the clogging or air bubbles. A suction outlet 42 is formed at one end of the suction flow path 4, to which a negative pressure source, such as a vacuum pump, is connected, while the other end of the suction flow path 4 is connected to the flow path 3 at a communication opening 41.

Figure 8:
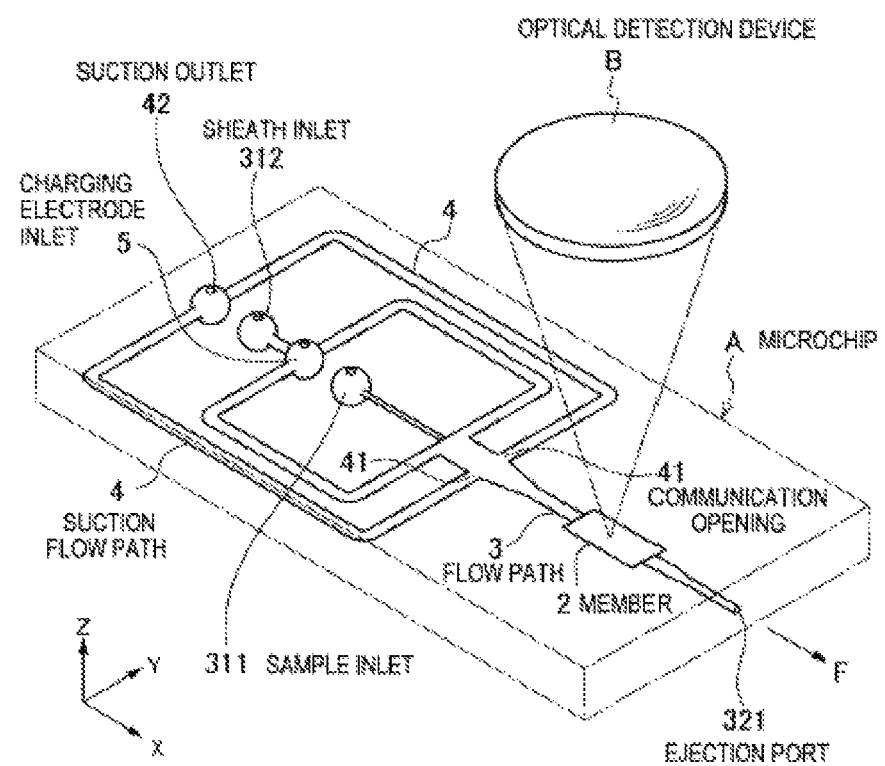
FIG. 8 is a schematic view illustrating a specific example of an embodiment of the composite structure according to the present technology.

The micro-particles are caused to flow through the flow path 3 such that the micro-particles are arranged in a row in the formed three-dimensional laminar flow, and are fed to a light irradiated portion that is irradiated by an optical detection device B. The optical detection device B includes: an irradiation system that includes a laser light source, a condenser lens that focuses/irradiates a laser beam with respect to the micro-particles, a dichroic mirror, a bandpass filter and the like; and a detection system that detects light to be measured that is emitted from the micro-particles by irradiation of the laser light. The detection system is formed by, for example, a photo multiplier tube (PMT), an area imaging device, such as a charge coupled device (CCD) or a complementary metal oxide semiconductor (CMOS) element, and the like. Note that, in FIG. 8, only the condenser lens is shown as the optical detection device B. Further, FIG. 8 shows a case in which the irradiation system and the detection system are formed using a same optical path. However, the irradiation system and the detection system may be formed using separate optical paths.

The light to be measured that is detected by the detection system of the optical detection device B is light emitted from the micro-particles by irradiation of measurement light. For example, forward scattered light, side scattered light, scattered light from Rayleigh-scattering, Mie-scattering or the like, and fluorescence can be used. These types of light to be measured are converted into electrical signals, and optical characteristics of the micro-particles are determined based on the electrical signals.

The sample liquid that has passed through the light irradiated portion is discharged to a space outside the microchip A from an ejection port 321 that is provided on one end of the flow path 3. At this time, if the microchip A is vibrated by a vibrating element, the sample liquid can be discharged to the space outside the microchip A as liquid droplets containing the micro-particles. An electric charge is applied to the discharged liquid droplets by an electrode inserted in a charging electrode inlet 5.

In the space outside the microchip A, a pair of electrodes are arranged to face each other such that the pair of electrodes sandwich the moving liquid droplets, along a movement direction of the discharged liquid droplets. The movement direction of the liquid droplets is controlled by an electric repulsive force (or a suction force) between the pair of electrodes and the liquid droplets. Thus, the micro-particles contained in the liquid droplets are separated and collected in accordance with the optical characteristics of the micro-particles.

In the microchip A, a section of the flow path 3 that forms the light irradiated portion that is irradiated by the optical detection device B is made of crystal, which is a material that has excellent optical transparency and small optical error. Therefore, irradiation efficiency of the laser beam onto the micro-particles is high and the light to be measured can be detected with a high degree of accuracy. It is therefore possible to separate and collect the micro-particles by accurately determining the optical characteristics of the micro-particles.

Further, only the light irradiated portion of the microchip A is made of crystal, which is expensive, and the other portions are made of thermoplastic resin, which is cheap and easily formed. Thus, it is also possible to reduce the cost of the entire microchip A. Note that the material of the member 2 is not limited to crystal as long as it is a material that has excellent optical transparency and small optical error.

Sections of the flow path 3 that are respectively formed in the substrate and the member 2 are linked and connected together without displacement occurring, by applying the above-described manufacturing method of the composite structure according to the present technology. With the manufacturing method of the composite structure according to the present technology, if the diameter of the flow path 3 is 100 micro meter, for example, it is possible to connect the sections of the flow path 3 at a positioning accuracy of several tens of micro meter or less.

As a result, in the microchip A, the three-dimensional laminar flow that is formed in the flow path 3 by the sample liquid and the sheath liquid can pass through the flow path 3 without disturbance at the joint between the section of the flow path 3 formed in the substrate and the section of the flow path 3 formed in the member 2. Accordingly, in the microchip A, it is possible to accurately measure the optical characteristics of the micro-particles while precisely matching a focal position of the laser beam in the light irradiated portion with a flowing position of the micro-particles. Further, it is possible to control the movement direction of the liquid droplets and to separate and collect the liquid droplets with high precision while stabilizing the shape and size of the liquid droplets discharged from the ejection port 321 to the space outside the microchip A.

It should be understood by those skilled in the art that various modifications, combinations, sub-combinations and alterations may occur depending on design requirements and other factors insofar as they are within the scope of the appended claims or the equivalents thereof.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The composite structure according to the present technology may also be configured as follows.

(1) A composite structure comprising:

at least two substrates which are made of thermoplastic resin and which are bonded by thermocompression; and at least one member which is made of a material whose heat distortion temperature is higher than a heat distortion temperature of the thermoplastic resin and which is inserted into a space formed in at least one of the substrates, wherein the member inserted in the space is fixed and held by wall surfaces which form the space of the substrates and which are thermally deformed by thermocompression.

(2) The composite structure according to (1), wherein a position of the member in the space is determined by the wall surfaces.

(3) The composite structure according to (1) or (2), wherein the member is positioned in the space such that regions that are respectively formed in at least one of the substrates and in the member are linked.

(4) The composite structure according to (3), wherein the composite structure is a microchip including a flow path which is formed as the regions and through which liquid passes.

(5) The composite structure according to (4), further comprising:

a light irradiated portion where light is irradiated onto one of the liquid that flows through the flow path and a sample contained in the liquid, wherein the light irradiated portion is formed by the member made of a material having optical transparency that is superior to that of the thermoplastic resin that forms the substrates.

In addition, the manufacturing method for a composite structure may also be configured as follows.

(1) A manufacturing method for a composite structure, comprising:

arranging at least two substrates which are made of thermoplastic resin and which have a space that is formed in at least one of the substrates;

inserting, into the space, at least one member that is made of a material whose heat distortion temperature is higher than a heat distortion temperature of the thermoplastic resin; and bonding the substrates by thermocompression and thereby causing wall surfaces, which form the space of the substrates and which are thermally deformed, to fix and hold the member inserted in the space.

(2) The manufacturing method according to (1), wherein in the step of causing the wall surfaces to fix and hold the member, a position of the member in the space is determined by the wall surfaces.

(3) The manufacturing method according to (1) or (2), wherein in the step of causing the wall surfaces to fix and hold the member, the member is positioned in the space such that regions that are respectively formed in at least one of the substrates and in the member are linked.

(4) The manufacturing method according to any one of (1) to (3), wherein in the step of causing the wall surfaces to fix and hold the member, the thermocompression of the substrates is performed at a temperature which is higher than the heat distortion temperature of the thermoplastic resin that forms the substrates and which is lower than the heat distortion temperature of the material that forms the member.

INDUSTRIAL APPLICABILITY

With the composite structure and the manufacturing method therefor according to the present technology, a plurality of members made of different materials can be easily and highly accurately positioned and combined, and an allowance for a tolerance of the members can be increased by combining the members utilizing thermal contraction of the members. Therefore, the present technology is useful when obtaining a structure by combining members that are made of different materials due to constraints of manufacturing processes, such as formation ease etc., and due to functional constraints, such as optical transparency etc. For example, the present technology can be used to form a high-performance structure for optical applications.

REFERENCE SIGNS LIST

A Microchip
B Optical detection device
11, 12 Substrate
13, 131, 132, 133, 134 Wall surface
14 Space
2 Embedded member
21 Engagement end
3 Flow path
31 Inlet port
311 Sample inlet
312 Sheath inlet
32 Discharge port
321 Ejection port
4 Suction flow path
41 Communication opening
42 Suction outlet
5 Charging electrode inlet

The invention claimed is:

1. A micro fluidic device comprising:
at least two substrates each comprising a thermoplastic resin;
a space provided in at least one of the substrates;
at least one member comprising a material having a heat distortion temperature higher than a heat distortion temperature of the thermoplastic resin and which is provided in the space,
wherein the at least one member is fixed within the space by at least one wall surface that is thermally deformed by thermocompression; and
a flow path formed between the at least two substrates, wherein at least a portion of the flow path is formed by the at least one member.

2. The micro fluidic device according to claim 1, wherein the at least one member includes a light irradiated portion where light is irradiated onto the portion of the flow path formed by the at least one member.

3. The micro fluidic device according to claim 1, wherein the at least one member includes at least one engagement end including a protrusion extending into a recess formed between the at least two substrates, and wherein the thermal deformation occurs around the protrusion.

4. The micro fluidic device according to claim 1, wherein at least one of the at least two substrates includes the at least one wall surface.

5. The micro fluidic device according to claim 1, wherein a first portion of the flow path is formed between the at least two substrates, and wherein a second portion of the flow path is formed by the at least one member.

6. The micro fluidic device according to claim 1, wherein the at least one member fluidly connects a first portion of the flow path to a second portion of the flow path.

7. The micro fluidic device according to claim 6, wherein the first portion of the flow path and the second portion of the flow path are formed between the at least two substrates and separated by the space in at least one of the at least two substrates.

8. The micro fluidic device according to claim 7, wherein the at least one member is located within the space to fluidly connect the first portion of the flow path to the second portion of the flow path.

9. The micro fluidic device according to claim 1, wherein the space separates a first portion of the flow path from a second portion of the flow path, and wherein the at least one member fluidly connects the first portion of the flow path with the second portion of the flow path.

10. The micro fluidic device according to claim 1, further comprising:
a light source that irradiates light to microparticles flowing in the flow path; and
a detector that detects optical characteristics of the microparticles.

11. The micro fluidic device according to claim 1, further comprising:
a pair of electrodes arranged to face each other configured to separate liquid droplets containing microparticles ejected from the substrates.

12. The micro fluidic device according to claim 11, further comprising:
an electrode that applies a charge to the liquid droplets in the flow path.

13. The micro fluidic device according to claim 1, wherein the at least one member includes at least one engagement end including a protrusion extending between the at least two substrates, and wherein the at least one member is fixed to the at least two substrates by the protrusion being held between the at least two substrates by the at least one wall surface that is thermally deformed by thermocompression.

14. The micro fluidic device according to claim 13, wherein at least one of the at least two substrates includes the at least one wall surface.

15. The micro fluidic device according to claim 13, wherein the at least one member includes a light irradiated portion where light can be irradiated onto one of a liquid that flows through the flow path and a sample contained in the liquid.

16. The micro fluidic device according to claim 13, wherein the at least one member comprises a material having a higher optical transparency than that of the thermoplastic resin.

17. The micro fluidic device according to claim 13, wherein each of a first end and a second end of the at least one member includes an engagement end including a protrusion, and wherein the at least one member is fixed to the at least two substrates by both of the protrusions being held between the at least two substrates by at least one wall surface that is thermally deformed by thermocompression.

18. The micro fluidic device according to claim 13, wherein the member comprises a glass material.

19. The micro fluidic device according to claim 13, wherein the at least two substrates overlap the protrusion at a recess formed between the at least two substrates.

20. A manufacturing method for a micro fluidic device comprising:
- arranging at least two substrates which are made of thermoplastic resin and which have a space that is formed in at least one of the substrates;
- inserting, into the space, at least one member comprising a material having a heat distortion temperature higher than a heat distortion temperature of the thermoplastic resin; and
- fixing the at least one member within the space by at least one wall surface that is thermally deformed by thermocompression; and
- forming a flow path between the at least two substrates, wherein at least a portion of the flow path is formed by the at least one member.

* * * * *